US012595502B2

(12) United States Patent
    Littleton et al.

(10) Patent No.:  US 12,595,502 B2
(45) Date of Patent:      Apr. 7, 2026

(54) METHOD AND SYSTEM FOR SELECTIVELY HARVESTING PRODUCTS FROM PLANT CELLS IN CULTURE

(71) Applicant: University of Kentucky Research Foundation, Lexington, KY (US)

(72) Inventors: John M. Littleton, Lexington, KY (US); Barbara Knutson, Lexington, KY (US); Luke Bradley, Lexington, KY (US); Stephen Rankin, Lexington, KY (US); Jan Smalle, Lexington, KY (US); Jasmina Kurepa, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 700 days.

(21) Appl. No.: 17/638,156

(22) PCT Filed: Aug. 31, 2020

(86) PCT No.: PCT/US2020/048847
    § 371 (c)(1),
    (2) Date: Feb. 24, 2022

(87) PCT Pub. No.: WO2021/042075
    PCT Pub. Date: Mar. 4, 2021

(65) Prior Publication Data
    US 2022/0298537 A1      Sep. 22, 2022

Related U.S. Application Data

(60) Provisional application No. 62/893,592, filed on Aug. 29, 2019.

(51) Int. Cl.
    *C12P 21/02*      (2006.01)
    *C07K 16/30*      (2006.01)
    *C12P 17/06*      (2006.01)

(52) U.S. Cl.
    CPC .............. *C12P 21/02* (2013.01); *C07K 16/30* (2013.01); *C12P 17/06* (2013.01); *C07K 2317/13* (2013.01); *C07K 2317/14* (2013.01); *C07K 2317/31* (2013.01)

(58) Field of Classification Search
    None
    See application file for complete search history.

(56) References Cited

U.S. PATENT DOCUMENTS

| | | | |
|---|---|---|---|
| 6,989,236 B1 | 1/2006 | Falcone et al. | |
| 7,547,520 B2 | 6/2009 | Falcone et al. | |
| 7,737,327 B2 | 6/2010 | Falcone et al. | |
| 2006/0236421 A1 | 10/2006 | Pennell et al. | |
| 2008/0319051 A1 | 12/2008 | Cohen | |
| 2009/0029392 A1 | 1/2009 | Josephson et al. | |
| 2012/0231971 A1 | 9/2012 | Choi et al. | |
| 2016/0040176 A1 | 2/2016 | Littleton et al. | |

OTHER PUBLICATIONS

Kurepa et al. The Plant Journal (2014) 77:443-453.*
Martin-Ortigose et al. Adv. Funct. Mater (2012), 22:3576-3582.*
Torney et al. Nature Nanotechnology (2007), 2:295-300.*
Qing, Lin-Sen et al. J. Sep. Sci (2011), vol. 34:3240-3245.*
Khan et al Materials Science & Engineering C C 106 (2020) 110190.*
Ruan et al., Imaging and Tracking of Tat Peptide-Conjugated Quantum Dots in Living Cells: New Insights into Nanoparticle Uptake, Intracellular Transport, and Vesicle Shedding, Journal of American Chemical Society, Nov. 6, 2007, vol. 129, No. 47, p. 14759-14766.
Atanasov AG, et al. Discovery and resupply of pharmacologically active plant-derived natural products: A review. Biotechnol Adv. Aug. 15, 2015. pii: S0734-9750(15)30027-36.
Wang JW, Wu JY. Effective elicitors and process strategies for enhancement of secondary metabolite production in hairy root cultures. Adv Biochem Eng Biotechnol. 2013; 134:55-89.
Littleton JM. The future of plant drug discovery. Expert Opinion on drug discovery. 1: 673-683, 2007.
Brown DP, Rogers DT, Gunjan SK, Gerhardt GA, Littleton JM Target-directed discovery and production of pharmaceuticals in transgenic mutant plant cells.J Biotechnol. 2016 20;238:9-14.
Villani ME, Morgun B, Brunetti P, Marusic C, Lombardi R, Pisoni I, Bacci C, Desiderio A, Benvenuto E, Donini M (2008) Plant pharming of a full-sized, tumor-targeting antibody using different expression strategies. Plant Biotechnology Journal 7(1): 59-72.
Bradley LH (2014) High-quality combinatorial protein libraries using the binary patterning approach. Methods Mol Biol, 1216:117-28.
Sapsford KE, Algar WR, Berti L, Gemmill KB, Casey BJ, Oh E, Stewart MH, Medintz IL (2013) Functionalizing Nanoparticles with Biological Molecules: Developing Chemistries that Facilitate Nanotechnology. Chem. Rev., 113: 1904-2074.

(Continued)

*Primary Examiner* — Medina A Ibrahim
(74) *Attorney, Agent, or Firm* — Stites & Harbison PLLC; Mandy Wilson Decker

(57) ABSTRACT

A method of recovering a product-of-interest from a plant or algal cell and a kit relating to the same are provided. The method of recovering a product-of-interest from a plant or algal cell includes (a) culturing a plant or algal cell that produces a product-of-interest in a culture medium; (b) adding functionalized nanoparticles to the culture medium, whereby the nanoparticles enter the plant or algal cell, bind the product-of-interest, and are extruded into the culture medium; (c) recovering the extruded nanoparticles from the culture medium; and (d) separating the product-of-interest from the extruded nanoparticles. The kit includes a plant or algal cell that produces a product-of-interest when in culture and a functionalized nanoparticle. Also provided is a method of separating plant or algal cells.

23 Claims, 2 Drawing Sheets

(56)                References Cited

OTHER PUBLICATIONS

Biju V (2014) Chemical modifications and bioconjugate reactions of nanomaterials for sensing, imaging, drug delivery and therapy. Chem. Soc. Rev., 43: 744-764.

Mosbach K, Ramström O (1996) The Emerging Technique of Molecular Imprinting and Its Future Impact on Biotechnology. Nature Biotechnol. 14: 163-170.

Díaz-García ME, Laiño RB (2005) Molecular Imprinting in Sol-Gel Materials: Recent Developments and Applications. Microchim. Acta, 149:19-36.

Lasáková M, Jandera P (2009) Molecularly imprinted polymers and their application in solid phase extraction. J. Sep. Sci. 32(5-6):799-812.

Joshi S, Rao A, Knutson BL, Rankin SE (2014) Interfacial Molecular Imprinting of Stober Particle Surfaces: A Simple Approach to Targeted Saccharide Adsorption. J. Colloid Interface Sci., 428:101-110.

Sun D, Hussain HL, Yi Z, Siegele R, Cresswell T, Kong L, Cahill DM (2014) Uptake and cellular distribution, in four plant species, of fluorescently labeled mesoporous silica nanoparticles, Plant Cell Rep. 33:1389-1402.

Slomberg DL, Schoenfisch MH (2012) Silica Nanoparticle Phytotoxicity to *Arabidopsis thaliana*, Environ. Sci. Technol. 46: 10247-10254.

Gogos A, Knauer K, Bucheli TD (2012) Nanomaterials in Plant Protection and Fertilization: Current State, Foreseen Applications, and Research Priorities, J. Agric. Food Chem. 60: 9781-9792.

Sakhtianchi R, Minchin RF, Lee K-B, Alkilany AM, Serpooshan V, Mahmoudi M (2013) Exocytosis of nanoparticles from cells: Role in cellular retention and toxicity, Adv. Colloid Interface Sci. 201-202: 18-29.

Liu J, Qiao SZ, Hu QH, Lu GQ (2011) Magnetic Nanocomposites with Mesoporous Structures: Synthesis and Applications, Small 7: 425-443.

Kurepa J, Nakanayashi R, Paunesku T, Suzuki M, Saito K, Woloschak GE and Smalle JA. Direct isolation of flavonoids from plants using ultra-small anatase TiO2 nanoparticles. (2014) Plant J. 77(3): 443-53.

Khan, et al., Nanoharvesting of bioactive materials from living plant cultures using engineered silica nanoparticles; Materials Science & Engineering C 106 (2020) 110190; pp. 1-11.

Khan, et al., Mechanism of Mesoporous Silica Nanoparticle Interaction with Hairy Root Cultures during Nanoharvesting of Biomolecules; Adv. Biology 2021, 5, 2000173; pp. 1-11.

* cited by examiner

METHOD AND SYSTEM FOR SELECTIVELY HARVESTING PRODUCTS FROM PLANT CELLS IN CULTURE

RELATED APPLICATIONS

This application is a national stage application, filed under 35 U.S.C. § 371, of International Patent Application No. PCT/US2020/048847, filed Aug. 29, 2020, which claims priority from U.S. Provisional Application Ser. No. 62/893,592, filed Aug. 29, 2019, the entire disclosures of which are incorporated herein by this reference.

GOVERNMENT INTEREST

This invention was made with government support under grant numbers R44AT008312 and 2R44AT008312-02 awarded by the National Institutes of Health. The government has certain rights in the invention.

TECHNICAL FIELD

The presently-disclosed subject matter generally relates to screening for and/or isolating a target product from a plant or algal cell culture without the need to destroy the plant or algal cell. In particular, certain embodiments of the presently-disclosed subject matter relate to use of a functionalized nanoparticle, on which specific oligopeptides have been conjugated, to screen for, capture, and/or isolate the target product.

BACKGROUND

Plants produce many useful products, which can include natural metabolites and exogenous products. Such products can have potent biological activity and economic import for the pharmaceutical, agrochemical, and nutrition industries. Plant cells in culture have also been used in the production of products-of-interest. However, the currently-available systems suffer from the drawback that "harvesting" the products requires the destruction of the plant cell. Since plant cells generally grow slowly in culture, destruction of the plant cell results in an inefficient "batch system," with prolonged down time as new cultures are established. In addition, solvent-based approaches to extraction of products from plant cells can involve use of large amounts of solvents and generates a great deal of chemical waste.

Accordingly, there remains a need for efficient systems and methods to extract products-of-interest from plant cells.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a method comprising (a) culturing a plant or algal cell that produces a product-of-interest in a culture medium; (b) adding functionalized nanoparticles to the culture medium, whereby the nanoparticles enter the plant or algal cell, bind the product-of-interest, and are extruded into the culture medium; (c) recovering the extruded nanoparticles from the culture medium; and (d) separating the product-of-interest from the extruded nanoparticles. In some embodiments, the cell is a transgenic plant or algal cell. In some embodiments, the cell is a mutant plant cell. In some embodiments, the mutant cell overproduces the product-of-interest.

In some embodiments, the cell produces an exogenous polypeptide. In some embodiments, the cell produces an antibody. In some embodiments, the cell produces a monoclonal antibody. In some embodiments, the cell produces a monoclonal antibody directed against a tumor cell. In one embodiments, the cell produces mAbH10. In some embodiments, the product-of-interest is an alkaloid, a vinca alkaloid, a flavonoid, a phytoestrogen, or liquiritigenin. In some embodiments, the nanoparticle is a silica nanoparticle. In some embodiments, the nanoparticle is magnetized. In some embodiments, the nanoparticle is between about 20 and 300 nm. In some embodiments, the nanoparticle comprises a moiety that selectively binds the product-of-interest. In some embodiments, the moiety is an oligonucleotide that selectively binds the product-of-interest. In some embodiments, the oligonucleotide has the sequence of a binding site of the protein of interest. In some embodiments, the oligonucleotide is conjugated to the nanoparticle. In some embodiments, the oligonucleotide further comprises a fluorescent probe.

Also provided herein, in some embodiments, is kit including a plant or algal cell that produces a product-of-interest when in culture; and a functionalized nanoparticle. In some embodiments, the cell is a transgenic plant or algal cell. In some embodiments, the cell is a mutant plant cell. In some embodiments, the mutant cell overproduces the product-of-interest. In some embodiments, the cell is a transgenic plant or algal cell. In some embodiments, the cell is a mutant plant cell. In some embodiments, the mutant cell overproduces the product-of-interest.

In some embodiments, the cell produces an exogenous polypeptide. In some embodiments, the cell produces an antibody. In some embodiments, the cell produces a monoclonal antibody. In some embodiments, the cell produces a monoclonal antibody directed against a tumor cell. In one embodiments, the cell produces mAbH10. In some embodiments, the product-of-interest is an alkaloid, a vinca alkaloid, a flavonoid, a phytoestrogen, or liquiritigenin. In some embodiments, the nanoparticle is a silica nanoparticle. In some embodiments, the nanoparticle is magnetized. In some embodiments, the nanoparticle is between about 20 and 300 nm. In some embodiments, the nanoparticle comprises a moiety that selectively binds the product-of-interest. In some embodiments, the moiety is an oligonucleotide that selectively binds the product-of-interest. In some embodiments, the oligonucleotide has the sequence of a binding site of the protein of interest. In some embodiments, the oligonucleotide is conjugated to the nanoparticle. In some embodiments, the oligonucleotide further comprises a fluorescent probe.

Further provided herein, in some embodiments, is a method including (a) culturing a plant or algal cell that produces a product-of-interest in a culture medium; (b) adding functionalized nanoparticles to the culture medium, whereby the nanoparticles enter the plant or algal cell, bind the product-of-interest, and produce a detectable change in fluorescence after binding the product-of-interest; and (c) detecting the change in fluorescence from the functionalized nanoparticles within the cells. In some embodiments, the method further includes separating the plant or algal cells based upon the fluorescence thereof.

Further features and advantages of the presently-disclosed subject matter will become evident to those of ordinary skill in the art after a study of the description, figures, and non-limiting examples in this document.

DESCRIPTION OF EXEMPLARY EMBODIMENTS

Figure 1:
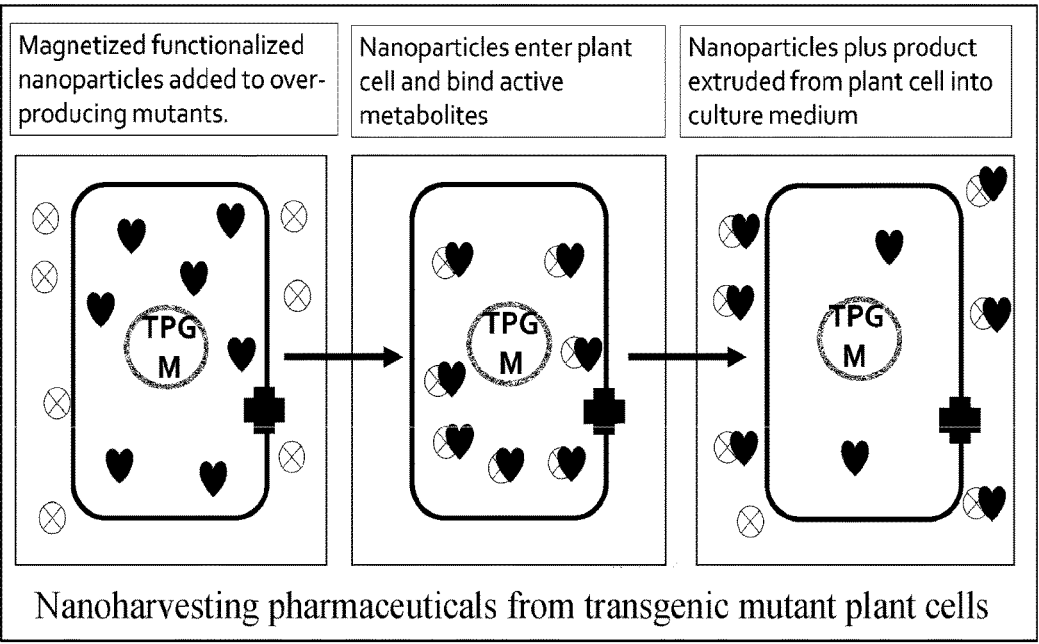
FIG. 1 shows a schematic illustrating the use of nanoparticles to "harvest" active metabolites from overproducing mutant plant cells. Mesoporus silica nanoparticles enter plant cells when these are cultured as "hairy roots" and are then extruded into the culture medium. By modifying the surface of these nanoparticles it is possible to increase the adsorption of specific types of metabolite, so that the nanoparticles translocate these metabolites from the interior of the cell to the culture medium. The first panel (left) shows nanoparticles ($\otimes$) added to the culture medium of a mutant plant cell culture that is overproducing metabolites ($\heartsuit$) with the "desirable" activity at the target protein. The middle panel shows the nanoparticles inside the plant cell adsorbing the metabolites with the desired activity, and the final panel (right) shows the extrusion of the nanoparticles together with the required product. The end result is that the product has been harvested from the plant cells without the necessity for solvent extraction or cellular disruption.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are described herein.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

While the terms used herein are believed to be well understood by those of ordinary skill in the art, certain definitions are set forth to facilitate explanation of the presently-disclosed subject matter.

As used herein, the term "about," when referring to a value or to an amount of mass, weight, time, volume, concentration or percentage is meant to encompass variations of in some embodiments ±5%, in some embodiments ±1%, in some embodiments ±0.5%, in some embodiments ±0.1%, and in some embodiments ±0.01% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

The presently-disclosed subject matter includes articles, systems, and methods for harvesting products-of-interest from plant cells in culture. In some embodiments, the articles include functionalized nanoparticles. These functionalized nanoparticles include nanoparticle having a surface which has been modified to increase the capture of a product-of-interest. For example, in some embodiments, the nanoparticle is coated with a product-binding moiety that binds the product-of-interest. Additionally or alternatively, in some embodiments, the product-binding moiety is conjugated to the nanoparticle. This conjugation may be through known strategies (see e.g., references 11 and 12, which are incorporated herein by reference), such as, but not limited to, through covalent attachment to the nanoparticle.

The nanoparticle includes any size and material suitable for uptake and expulsion by plant cells. In some embodiments, the nanoparticle includes a silica nanoparticle. Silica represents a relatively mature platform for engineering of particle features including particle diameter, pore size, pore structure, and surface functionalization. However, the disclosure is not limited to silica nanoparticles and explicitly includes other suitable nanoparticle materials, such as, but not limited to, other metal oxides (e.g., aluminum or titanium oxides), metals (e.g., copper), carbon-based materials (see e.g., reference 19, which is incorporated herein by reference), any other suitable nanoparticle materials utilized in plant or algal biotechnology, or a combination thereof. Suitable nanoparticle sizes include, but are not limited to, at least about 20 nm, up to about 300 nm, between about 20 nm and about 300 nm, between about 20 nm and about 250 nm, between about 20 nm and about 200 nm, between about 20 nm and about 150 nm, between about 30 nm and about 300 nm, between about 40 nm and about 300 nm, between about 50 nm and about 300 nm, between about 50 nm and about 250 nm, between about 100 nm and about 300 nm, between about 100 nm and about 250 nm, between about 100 nm and about 200 nm, about 150 nm, or any combination, sub-combination, range, or sub-range thereof. In some embodiments, for example, the nanoparticle is about 150 nm.

The product-binding moiety includes any moiety suitable for modification of the nanoparticle and binding with the product-of-interest. In some embodiments, the product-binding moiety selectively binds to the product-of-interest. Since molecules commonly cause their bioactivity by binding to target proteins, it is possible to bind the product-of-interest with an immobilized oligopeptides that represent the binding site of the product-of-interest. Accordingly, one suitable product-binding moiety includes an oligopeptide that selectively binds the product-of-interest. In some embodiments, the oligopeptide includes the sequence of a binding site of the product-of-interest. As will be appreciated by those skilled in the art, such sequences will vary depending upon the particular product-of-interest. While it is impractical to list each and every sequence corresponding to the various different products-of-interest, as will be appreciated by those skilled in the art, the sequence may be selected based on known affinity for the product-of-interest. Additionally or alternatively, the sequence may be optimized by generating libraries of sequences similar to a hypothesized binding site and screening for binding to the target product (see e.g., reference 10, which is incorporated herein by reference).

Other suitable product-binding moieties include, but are not limited to, synthetic binding sites created by introducing complementary functionality to the particle surface to bind the product-of-interest. These synthetic binding sites may be created using strategies such as molecular imprinting (see e.g., references 13-16, which are incorporated herein by reference). For example, in some embodiments, titanium may be used to bind catechol moieties of flavonoids (see e.g., Examples). Other examples of complementary functional groups include, but are not limited to, methoxyphenyl groups for binding methoxylated flavonoids, silica for binding amine groups in alkaloids, aminopropyl groups for hydrogen bonding with groups such as hydroxyl and carboxylate groups, and alkyl groups for binding to hydrophobic regions of target compounds.

In some embodiments, the functionalized nanoparticles are further modified to become a fluorescent indicator of ligand (e.g., product-of-interest) binding, facilitate recovery, and/or facilitate uptake and/or expulsion. For example, in some embodiments, the product-binding moiety is modified in any suitable manner to provide fluorescence and/or increased fluorescence following binding of the product-of-interest thereto. In one embodiment, a product-binding oligopeptide, or other product-binding moiety, is modified through attachment of a fluorescent probe thereto. Suitable probes include any probe that fluoresces upon structural, conformational, physical (e.g., charge), or other change in the product-binding moiety following binding of the product-of-interest. In another embodiment, the structure of the product-binding moiety is directly modified such that the product-binding moiety itself fluoresces upon binding to the product-of-interest. Accordingly, whether modified directly, through attachment of a probe, or both, when the product-of-interest binds to the modified product-binding moiety a resulting change in the product-binding moiety causes a change in the detectable fluorescence of the modified product-binding moiety.

Additionally or alternatively, in some embodiments, the functionalized nanoparticle is modified to facilitate recovery thereof. In some embodiments, for example, the functionalized nanoparticles are magnetized to facilitate their recovery from a medium (see e.g., reference 21, which is incorporated herein by this reference). Elution of the product-of-interest from these recovered nanoparticles provides functionalized nanoparticles that are free of the product-of-interest, and thus may be re-used. In some embodiments, the expulsion of nanoparticles from plant or algal cells may be enhanced by pre-loading the particles with factors known to induce exocytosis. Exocytosis inducing factors include, but are not limited to, calcium or polyethyleneimine (see e.g., reference 20, which is incorporated herein by this reference).

The functionalized nanoparticles are suitable for screening and/or harvesting products-of-interest, including high value pharmaceuticals and nutraceuticals produced in plant or algal cells. Such pharmaceuticals and nutraceuticals include, but are not limited to, any one or more of the products-of-interest disclosed herein. As used herein, the term "product-of-interest" is limited to a product that is produced by a plant or algal cell, including wild-type, transgenic, mutagenized, or other plant or algal cell, and which has a known target protein which confers a desired bioactivity. The desired bioactivity may be any suitable effect on living tissue, including, but not limited to, activity for diagnostic, prophylactic, therapeutic, medicinal, pharmacologic, and/or toxic purposes. For example, the product-of-interest may form a diagnostic agent, biologic, antibody, vaccine, antiviral, antibacterial, anti-cancer, therapeutic, chemotherapeutic, and/or pharmaceutical. As will be recognized by the skilled artisan upon study of the description herein, the product-of-interest can be of interest due to an ability to bind a human protein that is a therapeutic target, e.g., an agonist of a protein target. In this regard, oligonucleotides representing the binding site of the protein target can be functionalized to the nanoparticle to capture the product-of-interest.

In some embodiments, the product-of-interest is naturally produced by a plant or algal cell (e.g., natural metabolite). Examples of natural products that can be produced by plant or algal cells include, but are not limited to, alkaloids (such as vinca alkaloids, taxoids and nicotinic alkaloids) and flavonoids (such as phytoestrogens, including liquiritigenin, and anti-inflammatory and neuroprotective flavonoids such as rhamnetin). Alternatively, in some embodiments, the product-of-interest is a polypeptide or nucleotide produced by a transgenic plant or algal cell by design, such as in the case of a plant or algal cell expressing a foreign transgene that encodes a foreign polypeptide such as an antibody or vaccine. Such plant or algal cells can be generated using molecular biological techniques that are well-known to those of ordinary skill in the art. Examples of polypeptides that are useful to produce using a transgenic plant or algal cell include, for example, a monoclonal antibody directed against a tumor cell, such as mAbH10, which is produced in some embodiments (see e.g., reference 9, which is incorporated herein by this reference).

Also provided herein, in some embodiments, are methods for screening cells for products-of-interest, harvesting products-of-interest, and/or separating cells using the functionalized nanoparticles according to one or more of the embodiments disclosed herein. In some embodiments, the method includes (a) culturing a plant or algal cell that produces a product-of-interest in a culture medium; and (b) adding functionalized nanoparticles to the culture medium. Any suitable amount of functionalized nanoparticles may be added to the culture medium. In some embodiments, suitable amounts include, but are not limited to, at least 10 mg/ml, at least 20 mg/ml, at least 30 mg/ml, at least 40 mg/ml, at least 50 mg/ml, at least 100 mg/ml, at least 250 mg/ml, at least 500 mg/ml, at least 1000 mg/ml, up to 1000 mg/ml, between 10 mg/ml and 1000 mg/ml, between 50 mg/ml and 1000 mg/ml, between 100 mg/ml and 1000 mg/ml, between 50 mg/ml and 500 mg/ml, or any combination, sub-combination, range, or sub-range thereof. In some embodiments, lower concentrations of functionalize nanoparticles (e.g., up to 100 mg/ml, up to 50 mg/ml, up to 25 mg/ml, up to 10 mg/ml, or any combination, sub-combination, range, or sub-range thereof) stimulate growth of the plant or algal cells. Although described above with respect to specific concentrations and ranges, as will be appreciated by those skilled in the art, suitable amounts may differ based upon the specific nanoparticles and plant or algal cells involved and thus the disclosure is not so limited. After being added to the culture medium, the functionalized nanoparticles enter the plant or algal cell and bind the product-of-interest. In some embodiments, the functionalized nanoparticles enter plant or algal cells without or substantially without causing a loss of viability.

In embodiments where the functionalized nanoparticles are modified to include a fluorescent probe, the functionalized nanoparticles produce a detectable change in fluorescence after entering the cell and binding to the product-of-interest. This change in fluorescence, or lack thereof, indicates the presence or absence, respectively, of the product-of-interest inside the cells. Accordingly, in such embodiments, the method may include (c) intracellular screening of plant or algal cells for the product-of-interest through detection of the presence or absence of fluorescent changes. Additionally, in some embodiments, the method optionally includes (d) separating plant or algal cells in a fluorescent cell sorter based on the content and/or amount of the product-of-interest. For example, the functionalized nanoparticles may be used to select cells (e.g., wild-type, transgenic, mutant, etc.) based upon the amount of biosynthesis of the product-of-interest. Following the screening (c) and optional separating (d), the method may include (e) recovering the functionalized nanoparticles from the culture medium after extrusion from the cells. The recovery may be by any suitable technique, such as, but not limited to, magnetic separation when the functionalized nanoparticles are magnetized as discussed above. Depending on density, size and wetting, other techniques for recovery include centrifugation or flotation. Once recovered, the method may further include (f) separating and/or collecting the product-of-interest from the extruded nanoparticles (e.g., elution).

As will be appreciated by those skilled in the art, certain steps according to the method above are not required and may be omitted. For example, in some embodiments, it may be desirable to collect the product-of-interest without screening the plant or algal cells first. In such embodiments, the method includes (a) culturing a plant or algal cell that produces a product-of-interest in a culture medium; (b) adding functionalized nanoparticles to the culture medium; (c) allowing the functionalized nanoparticles to enter the plant or algal cell, bind the product-of-interest, and be extruded back into the culture medium; and (d) recovering the extruded nanoparticles from the culture medium; and (e) separating the product-of-interest from the recovered nanoparticles. As discussed above, in some embodiments, the functionalized nanoparticles enter plant or algal cells, bind the product-of-interest, and are extruded from the plant or algal cells with the bound product-of-interest without or substantially without causing a loss of viability.

By extruding the functionalized nanoparticles/product-of-interest without affecting the plant or algal cell viability according to one or more of the embodiments disclosed herein, the functionalized nanoparticles facilitate repeated harvesting of the product-of-interest from the same cells. This increases efficiency, reduces down time (e.g., the time in between harvesting when new cells are being cultured/grown), reduces response time (e.g., faster production from a reduced number of cells for urgent requirement, such as during an outbreak), and/or increases reproducibility. The separation of the product-of-interest from the functionalized nanoparticles also permits re-use of the functionalized nanoparticles, which further increases efficiency. Additionally or alternatively, the selective binding and removal of the product-of-interest by the functionalize nanoparticles simultaneously semi-purifies the product-of-interest during extrusion/extraction.

As used herein, the term "plant cell" refers to a cell from a plant that can be grown in culture and which produces a desired product that binds to a known target protein. This includes almost all plant derived pharmaceuticals, many agrochemicals and some nutritional products. Relevant species of plant cells that can be used in accordance with the methods disclosed herein include, but are not limited to, *Glycyrrhiza glabra* (licorice) and *Catharanthus roseus*. Additional examples of relevant species of plant cells which produce valuable bioactive metabolites include, but are not limited to, *Nicotiana tabacum* (tobacco), *Hypericum perforatum* (St John's wort), and *Lobelia cardinalis* (Cardinal flower).

As used herein, the term "algal cell" refers to a cell from an alga or algae that can be grown in culture and which produces a desired product that binds to a known target protein.

In some embodiments the plant or algal cell is a wild-type plant or algal cell that produces a natural product-of-interest. In some embodiments, the plant or algal cell is a transgenic plant or algal cell, engineered to produce a particular product-of-interest. In some embodiments, the plant or algal cell is a mutagenized plant or algal cell that overproduces a particular product-of-interest. The term "overproduce," when used in connection with a mutant plant or algal cell, refers to production levels of a product-of-interest, as compared to a non-mutant plant or algal cell from the same species. Such mutant plant or algal cell can be obtained, for example, using selection techniques to identify and obtain overproducing mutant plant or algal cells (see e.g., references 3-8, which are incorporated herein by reference). In some embodiments, the plant or algal cell can be obtained using methods described in U.S. patent application Ser. No. 14/821,461, which is incorporated herein by this reference.

Figure 2:
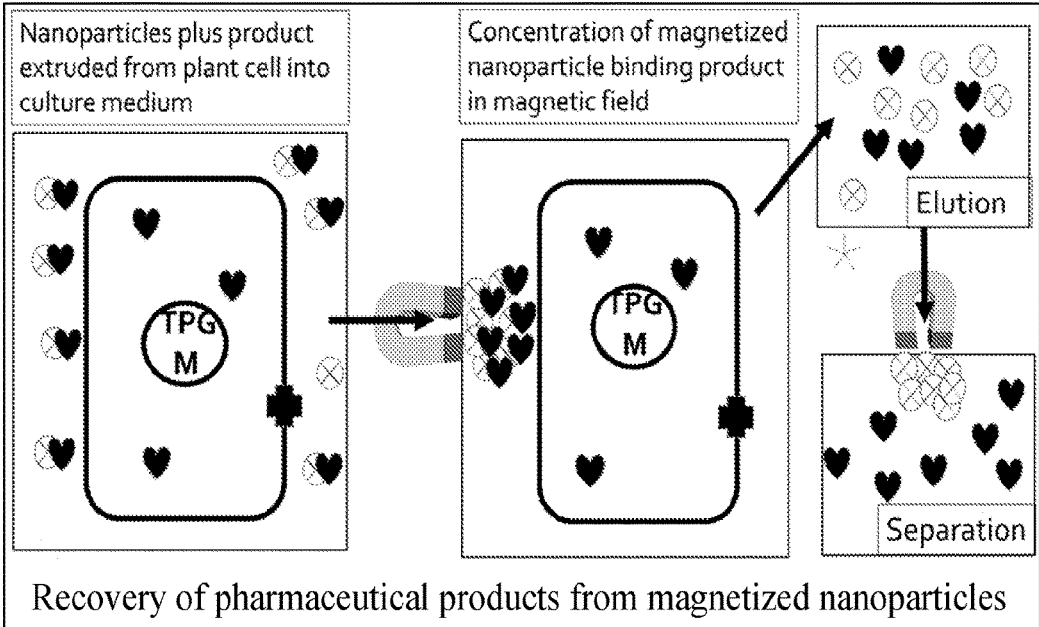
FIG. 2 shows a schematic illustrating harvesting active metabolites by separation of magnetized nanoparticles and elution of products. The utility of nanoharvesting is increased by using magnetized nanoparticles ($\otimes$) because these can readily be separated from other particulates in cell culture medium using a magnetic field. Once the magnetized nanoparticles and the adsorbed product ($\heartsuit$) have been recovered from the culture medium the product can be eluted and the nanoparticles again separated in a magnetic field. This recovers the product and the nanoparticles.

By way of an example, reference is made to FIG. 1, which illustrates the functionalized nanoparticles entering the plant cell where they bind active metabolites, and are thereafter extruded from the plant cell into the culture medium. As illustrated in FIG. 2, in some embodiments, the nanoparticles are magnetized, and can be readily collected from the culture medium. Thereafter, the product can be eluted and the nanoparticles can be separated again in a magnetic field, allowing the product to be collected and the nanoparticles to be recovered for future use. Furthermore, and with reference to FIG. 3, the plant cells can also be reused for repeated, or even continuous, harvesting of the product.

Further provided herein, in some embodiments, is a system for screening products-of-interest, harvesting products-of-interest, and/or separating cells. In some embodiments, the system includes functionalized nanoparticles according to one or more of the embodiments disclosed herein and culture medium for growing plant or algal cells. In some embodiments, the system also includes the plant or algal cells to be grown in the culture medium. As discussed above, these functionalized nanoparticles isolate and at least partially purify products-of-interest from plant cells without destroying the plant cells. By isolating and/or at least partially purifying the products-of-interest from the plant cells without destroying the plant cells the presently-disclosed subject matter provides a continuous harvesting system which, as opposed to existing systems, does not require destruction of the plants.

In some embodiments, the articles, methods, and systems disclosed herein are useful for biosynthetic production and harvesting of bioactive metabolites and exogenous polypeptides that are too complex for efficient production by chemical synthesis or other previously-disclosed methods. In some embodiments, the articles, methods, and systems disclosed herein enable more efficient use of the capability of plant cells for the discovery and production of products by biosynthesis. This biosynthesis requires only the chemicals obtained from plant cell culture medium and the product yields can be increased by the use of mutant plant cells. Additionally, rather than extracting active metabolites from plant cells using organic solvents, these metabolites, or products-of-interest, can be "harvested" by the functionalized nanoparticles disclosed herein. After harvesting, the plant cells remain viable, and can be re-used for repeated nanoharvesting, making the environmental impact close to zero. Furthermore, the selectivity of harvesting for the desired product can be engineered into the nanoparticles by imprinting the chemical structure of the product on the nanoparticles.

The presently-disclosed subject matter is further illustrated by the following specific but non-limiting examples. The following examples include prophetic examples.

EXAMPLES

Nanoharvesting of pharmaceuticals from plant cells. The uptake of ultra-small titania nanoparticles into roots of the model plant *Arabidopsis thaliana* has been described. These nanoparticles were then extruded from the roots and shown to have adsorbed flavonoids from the plant. "Nanoharvesting" was the term coined to describe this process.

Figure 3:
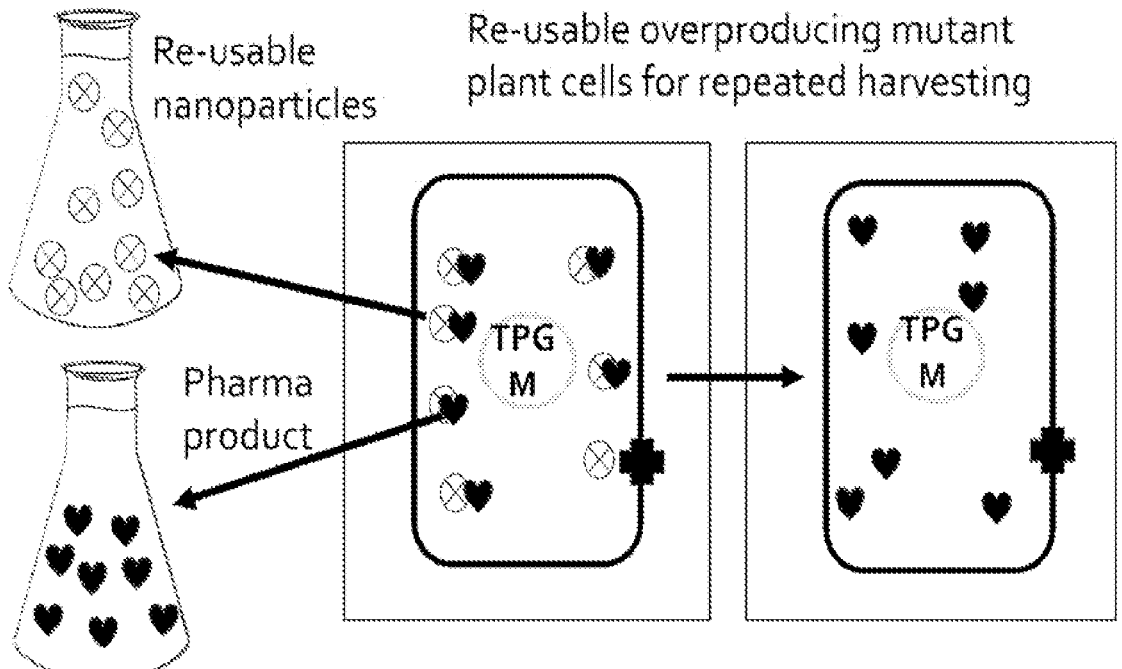
FIG. 3 shows a schematic illustrating the re-use of both the mutant plant cells and the functionalized nanoparticles for repeated harvesting of products. The sequence for nanoharvesting recovers both the desired pharmaceutical product ($\heartsuit$) and nanoparticles ($\otimes$) that are no longer binding this product. If the elution procedure is chosen so that it does not affect the functionalization of the nanoparticles, then these can be re-used for harvesting. Similarly the uptake and extrusion of the nanoparticles does not seem to damage the plant cells and these continue to produce the desired product. Therefore, both the mutant transgenic plant cells and the nanoparticles can be used for repeated (or even continuous) harvesting of product. This provides a very environmentally friendly technology with minimal waste.

The present inventors have conceived a method and system for using versatile nanoparticles that have been functionalized to harvest products-of-interest from plant cell cultures. Reference is made to FIGS. 1-3, which provide an illustration of how the method and system operates.

Example 1—Flavonoid

The biosynthesis of flavonoids in mutant hairy roots of *Solidago nemoralis* (gray goldenrod) was used as an example. These flavonoids include methoxylated quercetins with agonist activity at the alpha7-subtype of nicotinic receptors, which have potential therapeutic value anti-inflammatory agents as a result.

The first step in nanoharvesting these products was to functionalize silica nanoparticles for increased adsorption of quercetin-like flavonoids. To this end magnetic mesoporous silica nanoparticles were synthesized by templating with the surfactant cetyltrimethylammonium bromide (CTAB) and functionalized with titanium (Ti) using Ti(IV) ethoxide (TEO). Particle size was controlled by Pluronic surfactant F127. The resulting nanoparticles were spherical with average diameter <200 nm. This functionalization increased the capacity of the nanoparticles to adsorb quercetin by at least two orders of magnitude up to a maximum of 232 mg quercetin/g nanoparticles. The nanoparticles were also functionalized using aminopropyltriethoxysilane to impart aminopropyl functionality to their surfaces. This is hypothesized to enhance their uptake in plant cells. These nanoparticles were taken up by *S. nemoralis* hairy roots in culture with the smaller nanoparticles found in clusters throughout the cells and larger nanoparticles localized closer to the cell wall (but still within the cells).

After 24 h, nanoparticles on which flavonoids were adsorbed could be recovered from the medium. This is facilitated by magnetization of nanoparticles which allows their separation in a magnetic field. The flavonoids could then be eluted from the nanoparticles using citric acid in ethanol and recovered. Chemical and pharmacological analysis indicated that nanoharvesting obtained essentially the same flavonoids, with the same pharmacological activity as were obtained by solvent extraction.

This series of experiments shows that nanoharvesting of flavonoids from plant cell cultures is a useful alternative to solvent extraction, but there are other advantages of this approach also. First, the plant cell cultures are re-usable for subsequent harvests, whereas they are killed by solvent extraction. Thus, the hairy root cultures of *S. nemoralis* were viable and continued normal growth following nanoparticle exposure. Low concentrations of nanoparticles (10 mg/ml) actually stimulated growth of the hairy root cultures, and even very high nanoparticle concentrations (1000 mg/ml)

did not diminish their viability. In addition, hairy root cultures continued to synthesize normal levels of flavonoids when tested 4 days after exposure to nanoparticles, indicating that repeated or continuous harvesting can be conducted.

This is particularly important for plant cells in this technology because they are commonly relatively slow growing and, if they are transformed or mutated, are expensive to produce. Not only are the plant cells re-usable, it is highly likely that the nanoparticles are also re-usable. The elution of flavonoids using citric acid in ethanol preserves the adsorption properties of titania for flavonoids, so that the nanoparticles can be recycled into the plant cell cultures after removal of the flavonoids.

Example 2—Selective Nanoharvesting

In the flavonoid example above, the functionalized nanoparticles harvest a mixture of flavonoids from the plant cells, only some of which have the required pharmacological activity. In order to use plant metabolites as therapeutic agents it is usually necessary to separate them from inactive or toxic metabolites. Conventionally, this would be by solvent-based extraction and separation, followed by chromatographic or affinity column separation. A much greener approach would be functionalize nanoparticles further, so that they adsorb and harvest only the desired metabolites. This provides a one-step process that would be highly efficient as a means of generating semi-pure plant metabolites for pharmaceutical use.

There are essentially two approaches—either nanoparticles can be functionalized for selectivity toward a chemical structure, or they can be functionalized for selectivity based on ligand binding sites. The methoxylated flavonoids used as an example of nanoharvesting above could also be used as examples of both approaches to selective nanoharvesting. In order to harvest these flavonoids specifically, the structure of 7-methoxylated quercetin would be imprinted into the titania surface of the nanoparticles with specific reactive groups engineered into the surface to increase selectivity of adsorption. As an alternative, the specific pharmacology of these flavonoids could be exploited for selective nanoharvesting. Since they act as agonists at the alpha7-nicotinic receptor they would be selectively removed by nanoparticles bearing oligopeptides representing the binding site on this receptor protein.

The use of transgenic mutant plant cells allows plant cells to be directed as to what type of pharmacological activity is desired for production. It differs radically from conventional approaches to plant drug discovery in that it allows access to the whole genomic capability of a plant species to generate novel medicines. It is a rapid and inexpensive biosynthetic alternative to combinatorial chemistry. The addition of selective nanoparticle harvesting to this approach is a major advance in making it both commercially viable, and chemically even greener. With re-usable nanoparticles and repeated or continuous harvesting of specific products from plant cells cultured in bioreactors, the technology can be scaled up for industrial use, and requires only the raw materials in plant cell culture with minimal chemical or biological waste. The integrated technology therefore provides a green alternative to chemical synthesis, and to chemical extraction and separation. It could make plants once again a major source of medicines, a position they have occupied throughout most of human history. The examples below illustrate uses of this selective nanoharvesting technology based on target proteins.

Example 3—Phytoestrogenic Flavonoids

Phytoestrogenic flavonoids are plant flavonoids that activate human estrogen receptors (ERs). The major plant sources are soybean (genistin), licorice root (liquiritigenin), and hops (prenyl naringenin). Their major uses are as "estrogen supplements" in menopause for which the world market in 2014 was $3.77 Bn. In the US, the market is dominated by soybean products, whereas in Asia, licorice root is more prevalent.

Liquiitigenin (from licorice), is highly selective for ERbeta (rather than ERalpha) providing therapeutic advantages (e.g., a reduced risk of hormone responsive breast cancer). Synthetic ERbeta selective agonists, are mostly based on modifications of the structure of estradiol. For example, Novo-nordisk has one of these in phase II trials. These synthetics will almost certainly be marketed mainly as hormone replacement therapy in menopause (although there are other indications also). Selective ERbeta-selective products from plants should compete with these synthetic hormone replacement treatments.

Mutant licorice root cultures can be used to generate high levels of liquiritgenin (and other ERbeta-selective flavonoids) that can be harvested by functionalized nanoparticles. More specifically, liquiritigenin may be harvested from overproducing mutant cultures of licorice root by selective binding to the ERbeta ligand-binding oligopeptide conjugated to nanoparticles.

Example 4—Cytotoxic Alkaloids

Cytotoxic alkaloids used in cancer chemotherapy are among the most valuable natural products produced in plants, with total sales estimated at well over $5 Bn. The two main classes are the vinca alkaloids (sales currently around $100M/year and declining slowly) and Paclitaxel derived from *Taxus* alkaloids produced in cell cultures of *Taxus baccata*. Paclitaxel is now the most commercially successful anti-cancer treatment with total sales reaching $3.7 Bn in 2012. The vinca and *Taxus* alkaloids both target human tubulin.

Chemotherapeutic vinca alkaloids may be produced from overproducing mutant cultures of *Catharanthus roseus*. These alkaloids may be harvested by affinity to nanoparticles bearing oligopeptides representing their binding sites on human tubulin.

Example 5—Recombinant Polypeptides

Recombinant polypeptides, referred to in some cases as "biologic" medicines, are a fastest growing sector of the pharmaceutical market. Monoclonal antibodies that are an important class of biologics. Since the commercialization of the first therapeutic monoclonal antibody product in 1986, this class of biopharmaceutical products has grown rapidly. By 2014, forty-seven monoclonal antibody products had been approved in the US or Europe for the treatment of a variety of diseases, including several types of cancer. Subsequently many of these products have also been approved for global markets. At the current approval rate of ~ four new products per year, at least 70 monoclonal antibody products will be on the market by 2020, and combined world-wide sales will be nearly $125 Bn.

A significant part of the cost of monoclonal antibodies as "biologic" medicines is in their production which, by definition, must be in biological tissue. Currently most monoclonals are still produced in transgenic mammals or mammalian cells, but this has the risk that mammalian pathogens (including prions) may contaminate the purified product. Production in transgenic bacterial or yeast cells runs a similar (but reduced risk) and all these methods require very expensive separation and purification steps to maintain safety.

Production of foreign polypeptides in plant cells would be safer because plant pathogens are rarely pathogenic to humans. Plant cell production should also be less expensive. This has resulted in major research efforts to produce antibodies in transgenic plants, usually *Nicotiana* species, where production of Ebola serum in *N. benthamiana* plants was a recent well-publicized example in the US. However, growing transgenic plants in open fields or greenhouses has its own major drawbacks including contamination with microbes and insects, variable growth rate and yields dependent on environment. In consequence, many companies are now considering polypeptide production in transgenic plant cells grown in sterile bioreactors. This has the advantage that only plant tissue is involved, and that conditions can be standardized to optimize production.

However, plant cell production suffers from the disadvantage that these transgenic plant cells are expensive to produce, and are generally slow-growing. Their destruction during extraction of the foreign polypeptides makes this approach less competitive. The ability to continuously and selectively harvest antibodies using functionalized nanoparticles, as disclosed herein, could increase the efficiency and lower costs for transgenic plant cells as production systems for biologic therapeutics.

In this example, plant cells generating a monoclonal antibody mAbH10 directed toward tumor cells are used. This antibody binds to epitopes on the cancer cells so as to reduce metastasis. The monoclonal antibody may be harvested from transgenic tobacco cell cultures expressing the gene for the antibody (mAbH10). Selective binding may be achieved using nanoparticles in which an oligopeptide mimicking the antibody-binding site on the antigen has been conjugated to the surface.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Atanasov A G, et al. Discovery and resupply of pharmacologically active plant-derived natural products: A review. Biotechnol Adv. 2015 Aug. 15. pii: S0734-9750 (15)30027-36
2. Wang J W, Wu J Y. Effective elicitors and process strategies for enhancement of secondary metabolite production in hairy root cultures. Adv Biochem Eng Biotechnol. 2013; 134:55-89
3. Littleton J M. The future of plant drug discovery. Expert Opinion on drug discovery. 1: 673-683, 2007
4. U.S. Pat. No. 6,989,236 for "Methods to identify plant metabolites," issued Jan. 24, 2006 to Falcone; Deane Louis (Lexington, KY), Littleton; John M. (Lexington, KY). Assignee: University of Kentucky Research Foundation (Lexington, KY).
5. U.S. Pat. No. 7,547,520 for "Methods to identify plant metabolites," issued Jun. 16, 2009 to Falcone; Deane Louis (Lexington, KY), Littleton; John M. (Lexington, KY). Assignee: University of Kentucky Research Foundation (Lexington, KY).
6. U.S. Pat. No. 7,737,327 for "Methods for screening for genes and small molecules that activate mammalian receptor proteins," issued Jun. 15, 2010 to Falcone; Deane Louis (Lexington, KY), Littleton; John M. (Lexington, KY).
Assignee: The University of Kentucky Research Foundation (Lexington, KY).
7. U.S. patent application Ser. No. 14/821,461 for "Target-directed biosynthesis of plant metabolites," with Notice of Allowance dated May 8, 2017, including inventors John Littleton, Dustin Brown, Samir Gunjan, Trent Rogers, Deane Falcone.
Assignee: Naprogenix Inc.
8. Brown D P, Rogers D T, Gunjan S K, Gerhardt G A, Littleton J M Target-directed discovery and production of pharmaceuticals in transgenic mutant plant cells. J Biotechnol. 2016 20; 238:9-14
9. Villani M E, Morgun B, Brunetti P, Marusic C, Lombardi R, Pisoni I, Bacci C, Desiderio A, Benvenuto E, Donini M (2008) Plant pharming of a full-sized, tumor-targeting antibody using different expression strategies. Plant Biotechnology Journal 7(1): 59-72.
10. Bradley L H (2014) High-quality combinatorial protein libraries using the binary patterning approach. Methods Mol Biol, 1216:117-28.
11. Sapsford K E, Algar W R, Berti L, Gemmill K B, Casey B J, Oh E, Stewart M H, Medintz I L (2013) Functionalizing Nanoparticles with Biological Molecules: Developing Chemistries that Facilitate Nanotechnology. Chem. Rev., 113: 1904-2074.
12. Biju V (2014) Chemical modifications and bioconjugate reactions of nanomaterials for sensing, imaging, drug delivery and therapy. Chem. Soc. Rev., 43: 744-764.
13. MosbachK, Ramström O (1996) The Emerging Technique of Molecular Imprinting and Its Future Impact on Biotechnology. Nature Biotechnol. 14: 163-170
14. Díaz-García M E, Laíño R B (2005) Molecular Imprinting in Sol-Gel Materials: Recent Developments and Applications. Microchim. Acta, 149:19-36.
15. Lasáková M, Jandera P (2009) Molecularly imprinted polymers and their application in solid phase extraction. J. Sep. Sci. 32(5-6):799-812.
16. Joshi S, Rao A, Knutson B L, Rankin S E (2014) Interfacial Molecular Imprinting of Stöber Particle Surfaces: A Simple Approach to Targeted Saccharide Adsorption. J. Colloid Interface Sci., 428:101-110.
17. Sun D, Hussain H L, Yi Z, Siegele R, Cresswell T, Kong L, Cahill D M (2014) Uptake and cellular distribution, in four plant species, of fluorescently labeled mesoporous silica nanoparticles, Plant Cell Rep. 33:1389-1402.
18. Slomberg D L, Schoenfisch M H (2012) Silica Nanoparticle Phytotoxicity to *Arabidopsis thaliana*, Environ. Sci. Technol. 46: 10247-10254.
19. Gogos A, Knauer K, Bucheli T D (2012) Nanomaterials in Plant Protection and Fertilization: Current State, Foreseen Applications, and Research Priorities, J. Agric. Food Chem. 60: 9781-9792.
20. Sakhtianchi R, Minchin R F, Lee K-B, Alkilany A M, Serpooshan V, Mahmoudi M (2013) Exocytosis of nanoparticles from cells: Role in cellular retention and toxicity, Adv. Colloid Interface Sci. 201-202: 18-29.

21. Liu J, Qiao S Z, Hu Q H, Lu G Q (2011) Magnetic Nanocomposites with Mesoporous Structures: Synthesis and Applications, Small 7: 425-443.
22. Kurepa J, Nakanayashi R, Paunesku T, Suzuki M, Saito K, Woloschak G E and Smalle J A. Direct isolation of flavonoids from plants using ultra-small anatase TiO$_2$ nanoparticles. (2014) Plant J. 77(3): 443-53.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for harvesting a product-of-interest from a plant cell, comprising:
   (a) in a culture medium, culturing a plant cell that produces a product-of-interest;
   (b) adding functionalized nanoparticles to the culture medium, whereby the nanoparticles enter the plant cell, bind the product-of-interest, and are extruded into the culture medium, wherein the functionalization enhances the nanoparticle entry into the plant cell, the nanoparticle binding selectivity for the product-of-interest produced by the plant cell, and the nanoparticle extrusion into the culture medium;
   (c) recovering the extruded functionalized nanoparticles from the culture medium; and
   (d) separating the product-of-interest bound to the extruded functionalized nanoparticles; wherein the nanoparticles are mesoporous silica nanoparticles between 100 nm and 200 nm in diameter.

2. The method of claim 1, wherein the plant cell is a transgenic plant cell.

3. The method of claim 2, wherein the plant cell produces an exogenous polypeptide.

4. The method of claim 2, wherein the plant cell produces an antibody.

5. The method of claim 2, wherein the plant cell produces a monoclonal antibody.

6. The method of claim 2, wherein the plant cell produces a monoclonal antibody directed against a tumor cell.

7. The method of claim 6, wherein the plant cell produces mAbH10.2.

8. The method of claim 1, wherein the plant cell is a mutant plant cell.

9. The method of claim 8, wherein the mutant plant cell overproduces the product-of-interest.

10. The method of claim 1, wherein the product-of-interest is an alkaloid.

11. The method of claim 1, wherein the product-of-interest is a vinca alkaloid.

12. The method of claim 1, wherein the product-of-interest is a flavonoid.

13. The method of claim 1, wherein the product-of-interest is a phytoestrogen.

14. The method of claim 1, wherein the product-of-interest is liquiritigenin.

15. The method of claim 1, wherein the nanoparticle is magnetized.

16. The method of claim 1, wherein the nanoparticles are about 150 nm in diameter.

17. The method of claim 1, wherein the nanoparticle comprises a moiety that selectively binds the product-of-interest.

18. The method of claim 17, wherein the moiety is an oligonucleotide that selectively binds the product-of-interest.

19. The method of claim 18, wherein the oligonucleotide has the sequence of a binding site of the protein of interest.

20. The method of claim 18, wherein the oligonucleotide is conjugated to the nanoparticle.

21. The method of claim 18, wherein the oligonucleotide further comprises a fluorescent probe.

22. A method for identifying a plant cell producing a product-of-interest, comprising:
   (a) in a culture medium, culturing plant cells;
   (b) adding functionalized nanoparticles to the culture medium, whereby the nanoparticles enter the plant cells, bind a product-of-interest, and produce a detectable change in fluorescence after binding the product-of-interest, wherein the functionalization enhances the nanoparticle entry into the plant cells and nanoparticle binding selectivity for the product-of-interest produced by the plant cells; and
   (c) detecting the change in fluorescence from the functionalized nanoparticles within the plant cells, thereby identifying a plant cell producing the product of interest; wherein the nanoparticle is a mesoporous silica nanoparticle with pore diameter between 100 nm to 200 nm.

23. The method of claim 22, further comprising separating the plant cells based upon the detected change in fluorescence thereof.

* * * * *